(12) United States Patent
Banerjee et al.

(10) Patent No.: US 7,118,882 B2
(45) Date of Patent: Oct. 10, 2006

(54) PROCESS FOR THE PREPARATION OF GALLIC ACID BY CO-CULTURE

(75) Inventors: Rintu Banerjee, Kolkata (IN); Gargi Mukherjee, West Bengal (IN)

(73) Assignee: Indian Institute of Technology an Indian Institute of Kharagpur, West Bengal (IN)

(*) Notice: Subject to any disclaimer, the term of this patent is extended or adjusted under 35 U.S.C. 154(b) by 86 days.

(21) Appl. No.: 10/481,070

(22) PCT Filed: Jun. 24, 2002

(86) PCT No.: PCT/IN02/00137

§ 371 (c)(1),
(2), (4) Date: Aug. 5, 2004

(87) PCT Pub. No.: WO03/000912

PCT Pub. Date: Jan. 3, 2003

(65) Prior Publication Data

US 2004/0253694 A1    Dec. 16, 2004

(30) Foreign Application Priority Data

Jun. 22, 2001    (IN) .............................. 344/CAL/01

(51) Int. Cl.
*C12P 39/00* (2006.01)
*C12P 1/02* (2006.01)
(52) U.S. Cl. ........................ 435/42; 435/171
(58) Field of Classification Search .................... None
See application file for complete search history.

(56) References Cited

FOREIGN PATENT DOCUMENTS

| EP | 0339011 | 10/1989 |
|----|---------|---------|
| JP | 50 025786 | 3/1975 |
| SU | 843992 | 7/1981 |
| SU | 114636323 | 3/1985 |
| SU | 316453 | 9/2002 |

OTHER PUBLICATIONS

Kar B. et al. "Microbial production of gallic acid by modified solid state fermentation". Journal of Industrial Microbiology & Biotechnology, 1999, 23: 173-177, entire document.*

Pourrat H. et al. "Production of gallic acid from tara by a strain of spergillus niger". J. Ferment. Technol., 1985, 63(4): 401-403. entire document.*

Filamentous Fungi, American Type Culture Collection (ATCC), 1996, 19th Edition, pp. 60-61. (pp. 1-4 including cover pages).*

Shantha T. "Fungal degradation of aflatoxin B1", Nat. Toxins, 1999, 7(5): 175-178. (abstract only, pp. 1-2).*

* cited by examiner

*Primary Examiner*—Sandra E. Saucier
*Assistant Examiner*—Satyendra K. Singh
(74) *Attorney, Agent, or Firm*—Venable LLP; Marina V. Schneller

(57) ABSTRACT

A process for the preparation of gallic acid using co-culture comprising providing a tannin-rich mixed substrate and a culture medium in fluid communication with each other, adding an induced innoculum comprising the fungi *Rhizopus oryzae* and *Aspergillus foetidus* to the substrate to obtain a fermented mass and gallic acid, extracting the gallic acid from the culture medium and the fermented mass using an organic solvent followed by evaporation of the organic solvent to obtain gallic acid.

15 Claims, No Drawings

PROCESS FOR THE PREPARATION OF GALLIC ACID BY CO-CULTURE

FIELD OF INVENTION

The invention relates to a process for the preparation of gallic acid by co-culture.

BACKGROUND OF THE INVENTION

Enzymes are specific proteins of living tissues that act as biocatalysts. Enzymes can accomplish those reactions at normal temperatures and pressure which would otherwise require expensive, energy demanding high temperature and/or pressures, or might not be possible at all. That is why, use of enzymes in industries is growing.

Many micro-organisms produce extra-cellular enzymes. They are chiefly hydrolasesand are involved primarily in the degradation of macromolecules to units capable of being taken into the living cell. With the versatility of micro-organisms in producing enzymes, new methods of making many industrially important chemicals are being explored.

Current developments in biotechnology are yielding new applications for microbial enzymes. In addition to the conventional applications in food and fermentation industries, microbial enzymes have attained significant role in biotransformations involving organic solvent media specially bioactive compounds. Alongwith the use of micro-organisms to produce biomass and microbial metabolites, microbial cells may be used to catalyse the conversion of a compound into a financially more valuable compound. Microbial processes have the advantage of specificity over the use of chemical reagents and of operating at relatively low pressures and temperatures.

An important enzyme having various industrial applications is tannase (tannin acyhydrolase), which is an extra-cellular enzyme falling under the hydrolase group of enzymes. Tannins are water-soluble, phenolic compounds with molecular weight (500–3000) that have the property of combining with proteins, cellulose, gelatin and pectin and can be classified into two distinct groups based on their structural configuration, the hydrolysable tannins and the condensed tannins.

Tannase is widely used in the food and chemical industries. Further, tannase is used in wine making where it hydrolyses chlorogenic acid and quinic acid, which favourably influences taste in, the process of wine making. Tannase also has potential in the manufacture of acorn wine. Tannase is also used alongwith lactase to treat grap juice and grape musts So as to remove phenolic substances for stabilization of the beverage. Tannase significantly reduces chill haze formation in beer. Discolouration and haze development during beer storage could be prevented by the enzymatic hydrolysis of wort phenolics with tannase.

Further, tannase is used in a preconversion treatment of fresh green tea flush in the production of instant tea. Tannase is also used in the determination of the structure of naturally occurring gallic acid esters.

Tannin acyl hydrolase commonly called tannase catalyzes, the hydrolysis of ester and depside bonds in such hydrolysable tannins as tannic acid, thereby releasing glucose and gallic acid. Gallic acid (3,4,5-Trihydroxybenzoic acid) finds various uses. In the pharmaceutical industry, gallic acid is used in the manufacture of trimethoprim. It is an antibacterial and is administered jointly with sulphonamide and together provide a broad spectrum action for medical treatment. TMP inhibits dihydrofolate reductase thereby blocking transformation of dihydrofolate to tetrahydrofolate. The consumption co-efficient of gallic acid in the manufacture of trimethoprim is 4.8. In the tannery industry gallic acid is used for homogenization of tannins, for the preparation of high grade leather tannins. Gallic acid is also used in the manufacture of ordinary writing inks and dyes, as a photographic developer. It also finds use in the enzymatic synthesis of gallic acid esters like propyl gallate, which is mainly used as an antioxidant in fats and oils, and also in beverages. It is used in the testing of mineral acids, dihydroxy acetone, and alkaloids, and as a synthetic intermediate for the production of pyrogallol which is used for the production of pyrogallol which is used for staining fur, leather, hair, etc.

Use of various fugal species to produce tannase is known in the art. A number of micro-organisms including bacteria like (*Bacillus pumilis, B. polymyxa, Corynebacterium* sp., *Klebsiella pneumoniae*) fungi (*Ascochyta* sp. *Penicillium* sp.) & yeasts (*Candida* sp.) have been reported to produce tannase.

Production of tannase by a strain of *Aspergillus niger* was reported by Tourrat et al. They found tannase activity was maximum when fermentation was carried out in submerged culture at a constant air flow. The enzyme activity was determined by gas chart method and the maximum enzyme activity was reported to be 5.5 n Kat/ml. R. Banerjee et.al, has reported the activity of tannase biosynthesis by a newly isolated *R. oryzae*. The experimental conditions were optimized in shake flask cultures. Maximum enzyme activity was found to be 6.12 U/ml.

R. Banerjee et al have also reported the production of tannase by solid state fermentation using *R. oryzae*.

Production of extracellular tannase by bacterial strains (*B. polymyxa, B. puminis, klebsiclla pnon* & *Corynebacterium*) within few hours of culture with simultaneous release of gallic acid & glucose has been reported by Deschamp et al.

Raj Kumar et al. have reported the isolation, purification and some properties of *Penicillium chrysogcnum* tannase.

The enzyme is stable up to 30 C. and within the pH range of 4.0–6.0 Km value was found to be $0.48 \times 10^{-4}$M with tannic acid as the substrate. Metal salts at 20 Mm inhibited with enzyme.

Continuous production of gallic acid from tara tannin in a bioreactor using *Penicilium chrysogenum* immobilized on sodium alginate & $CaCl_2$ is known from Yamada et al. They have also reported the use of tannase in wine making industry.

Not much is known about the biotransformation of tannins to gallic acid. The literature available mainly relates to chemical process wherein the yield of gallic acid is was very low. Kar, B. et al have reported the biotransformation of tannins to gallic acid by SSF and SmF process using gallo seed cover and *Rhizopus oryzae* as the raw material.

However, the processes of the art suffer from various drawbacks ie they require a long time and the yield reported is also low.

OBJECTS OF THE INVENTION

It is therefore an object of this invention to propose a process for the preparation of gallic acid using mixed culture process, which requires less time compared to conventional techniques.

It is a further object of this invention to propose a process for the preparation of gallic acid using mixed culture technique which gives better yield and employs a novel substrate.

DESCRIPTION OF THE INVENTION

Thus according to this invention is provided a process for the preparation of gallic using co-culture, comprising providing a tannin-rich mixed substrate and a culture medium in fluid communication with each other, adding an induced innoculum comprising the fungi *Rhizopus oryzae* and *Aspergillus foetidus* to the substrate to obtain a fermented mass and gallic acid, extracting the gallic acid from the culture medium and the fermented mass using an organic solvent followed by evaporation of the organic solvent to obtain gallic acid.

In accordance with this invention, the raw materials used as mixed substrates are myrobalan fruit powder (*Terminalia chebula*, seedless type, PUNJAB variety) and gallo seed cover powder (*Caesalpinia digyna*) in a proportion of 1:3 to 3:1. These are substrates rich in tannin. Myrobalan seed contains 33–45% tannin and gallo seed cover contains about 58% tannin. Two strains of the filamentous fungi *Rhizopus oryzae* (RO IIT RB13,NRRL-21498) and *Aspergillus foetidus* (GMRB013), isolated from the soil of IIT, Kharagpur Campus have been used. The organisms are maintained on 2% malt extract agar slant. A subculture of the microorganisms is done on slants. A malt extract agar (MEA) medium is sterilized and a portion of it is transferred into sterile test tubes and allowed to cool in slanting position.

After solidification, the sterile slants are inoculated with pure cultures of *Rhizopus oryzae* (RO III RB13), NRRL-21498) and *Aspergillus foetidus* (GMRR 013, MTCC 3557) and kept in an incubator. The slant cultures are then used for further work or stored. As tannase is an adaptive enzyme, a pre-induced innoculum for the culture is prepared wherein tannic acid in modified Czapekdox medium is sterilized and inoculated with a spore suspension prepared from the cultured slants. They are then kept in a BOD incubator under shaking, to produce the induced innoculum. For subsequent studies of MSSF (Modified Solid State Fermentation), this induced innoculum is used.

The two microorganisms were used together where the ratio of the organisms varied from 0.5:2 to 1:1, where the optimum ratio was 1:1. It was found in general, that upon carrying out the co-culture technique, the tannase and gallic acid produced was higher than that produced under pure culture conditions, and also the incubation period required was shorter.

Fermentation is carried out in batch process under modified solid state fermentation in a modified tray type reactor. The raw materials used as mixed substrates are myrobalan fruit powder and gallo seed cover powder taken in a proportion of 1:3 to 3:1. This substrate mixture is placed on the float of the tray reactor. The tray reactors ordinarily used are modified by providing a perforated float. This offers the unique advantages of greater heat dissipation during fermentation which prevents the biomass from getting denatured. Liquid modified Czapekdox medium in the ratio of 0.2:1 to 0.8:1 (solid-liquid ratio) is taken beneath the float in the tray. Czapekdox medium is modified by using tannic acid as the carbohydrate source, instead of glucose. Thus, the mixed substrate placed on the float comes in contact with the liquid medium in the tray. The modified tray reactor is then autoclaved. Fermentation of the substrates on the float is carried out by adding an appropriate amount of induced innoculum of *Rhizopus oryzae* and *Aspergillus foetidus,* ie by co-culture method about $1\times10^5$ to $2\times10^8$ spores per ml, preferably $2\times10^6$ spores per ml is added to 20 gms of the substrate. The micro-organizm added to the substrate converts the substrate into the desired product, which leaches into the liquid medium. The fermented material is removed, water is added and heated. It is then cooled to room temperature and gallic acid is extracted using an organic solvent such as diethyl ether and ethyl acetate.

The optimum conditions of pH, temperature, humidity and the effects of quantity of innoculum, particle size and moisture on the production of gallic acid have been evaluated.

The invention will now be explained in greater detail with the help of the following non-limiting examples:

EXAMPLE

Isolation of Tannase Producing Microorganisms

Two strains of filamentous fungi *Rhizopus oryzae* (RO IIT RB 13, NRRL-21498) and *Aspergillus foetidus* (GMRB013) were isolated from the soil of I.I.T., Kharagpur campus by a baiting technique. The organisms were maintained on 2% malt extract agar slant.

Subculture of Microorganisms on Slants 100 ml of malt extract agar (MEA) medium was sterilized. After sterilization, 5 ml of it was transferred into sterile test tubes and allowed to cool in slanting position. After solidification, the sterile slants were inoculated with pure cultures of *Rhizopus oryzae* RO IIT RB13, NRRL-21498) and *Aspergillus foetidus* (GMRB 013) in a 1:1 ratio by streaking and was kept in incubator at 30° C. for (72–96) hrs.

The slant cultures were then used for further work or stored in fridge at 4° C.

Preparation of Induced Innoculum

Tannase being an adaptive enzyme, pre-induced inoculum is required to be prepared. 50 ml of 2% tannic acid in Czapekdox medium was taken in 100 ml conical flasks. It was then sterilised at 121° C. for 15 mins and inoculated with 2 ml of spore suspension prepared from the cultured slants. They were then kept in BOD incubator at 30° C. under shaking condition for 72 hrs. For subsequent studies of SSF, this induced inoculum was used.

Modified Solid State Fermentation Using Mixed Substrates by Co-Culture Method

Fermentation was carried out in batch process under modified solid state fermentation in a modified tray type reactor.

The raw materials used as mixed substrates where myrobalan seed powder (*Terminalia chebula*) and gallo seed cover powder (*Caesalpinia digyna*) taken in a proportion of 1:3 to 3:1. This substrate mixture was placed on the float of the tray reactor. Liquid Czapek dox medium in the ration of 0.2:1 to 0.8:1 (solid-liquid ratio) is taken beneath the float in the tray. This kind of float with the substrate is kept above the liquid in the tray in order to carry out modified solid state fermentation. Thus, the mixed substrate placed on the float comes in contact with the liquid medium in the tray. The modified tray reactor is then autoclaved at 121° C. for 15 mins. Fermentation of the substrates on the float is carried out by adding $2\times10^6$ spores/ml of induced inoculum of *Rhizopus oryzae* and *Aspergillus foetidus* per 20 gms of substrate ie. By co-culture method. The microorganism added to the substrate converts the substrate into the desired product, which leaches into the liquid medium.

Gallic Acid Extraction

Gallic acid was isolated using the organic solvent ethyl acetate. The fermented material was removed, water added, and heated to about (60–70)° C. because gallic acid is soluble at this temperature, and not in cold water. Then it was cooled to room temperature. Organic solvent was then added to it and the whole mixture was taken in a separating funnel. The mixture was immediately mixed thoroughly by vigorous shaking. Gallic acid being soluble in organic solvent, comes into the organic phase and the rest of the matter remains in aqueous phase. The aqueous phase was discarded and the organic layer was collected. This process was continued till the entire gallic acid came out into the organic layer. The collected volume of organic layer was now taken for separation of gallic acid from ethyl acetate in the rotary vacuum evaporator. The pressure and temperature at which this separation was done was 200 mbar and 70° C. Alternatively, the ethyl acetate layer was extracted with diethyl ether, the ether layer was evaporated in a rotary evaporator to obtain pure gallic acid. The yield of the gallic acid obtained was found to vary from 65.4 to 94.8%. Studies were conducted for optimization of various environmental parameters for obtaining maximum gallic acid production.

Optimization of Physicochemical Parameters for Tannase and Gallic Acid Production by Modified Solid-State Fermentation The effect of the various environmental parameters on the production of tannase and gallic acid upon carrying out MSSF by both the organisms using mixed substrates under both pure culture and co-culture conditions was studied Effect of pH:—The effect of pH on production of tannase was studied by varying the intitial pH of the Czapekdox medium from 3.5 to 7.0. The optimum pH was found to be 5, at which tannase activity was 35.1 U/ml and gallic acid produced was 91.81%.

Effect of temperature:—The effect of temperature on tannase and gallic acid production was studied by varying the temperature in the humidity cabinet from 25° C. to 40° C. where the optimum temperature was found to be 30° C. The amount of tannase and gallic acid produced was 36.4 U/ml and 93.25% respectively.

Effect of humidity:—The effect of humidity on tannase production and % yield of gallic acid was studied by varying the humidity in the humidity chamber from 70% to 90% where the optimum lies between 80%. The amount of tannase and gallic acid produced was 36.4 U/ml and 93.25% respectively.

Effect of inoculum amount:—The optimum amount of inoculum required for the maximum tannase production was obtained after varying the amount of inoculum from 1 ml to 4 ml with optimum at 3 ml.

Effect of moisture:—To study the effect of moisture on production of tannase, addition of Czapekdox medium to myrobalan substrate was varied from 0.2:1 to 0.8:1 where optimum lies to 0.4:1. Tannase and gallic acid produced were 35.3 U/ml and 92.41 respectively at this moisture condition. An incubation period of 48h was found to be the optimum for Gallic acid production by co-culture method using mixed substrates, giving a tannase activity of 33.1 U/ml.

A comparison between pure culture and co-culture methods shows the (following advantages of the co-culture method as highlighted in Table 1.

| CONDITIONS | Pure Culture with Rhizopus Oryzae using Single Substrate (Myrobalam) | Pure Culture with Aspergillus Foetidus using single Substrate (Myrobalam) | Co-Culture with Rhizopus Oryzae & Aspergillus Foetidus Using mixed Substrates |
|---|---|---|---|
| 1) Temperature | (25–40)° C. | (25–40)° C. | (25–40)° C. |
| 2) PH | 3.5–7 | 3.5–7 | 3.5–7 |
| 3) Humidity | (70–90)% | (70–90)% | (70–90)% |
| 4) Incubation period | 24–96 hrs | 24–96 hrs | 24–96 hrs |
| 5) Moisture (Solid-Liquid Ratio) | 1:0.25–1:1.5 | 1:0.25–1:1.5 | 0.2:1–8:1 |
| 6) Reactor Type | Tray | Tray | Modified Tray |
| 7) Gallic Acid | 44–87.67% | 51.19–92.45% | 65.42–94% |

We claim:

1. A process for the preparation of gallic acid comprising:
   providing a tannin-rich mixed substrate and a culture medium, in a liquid medium;
   adding an induced innoculum comprising the fungi *Rhizopus oryzae* and *Aspergillus foetidus* to said substrate to obtain a fermented mass and gallic acid;
   extracting gallic acid from the culture medium and the fermented mass using an organic solvent; and
   evaporating the organic solvent to obtain gallic acid.

2. The process as claimed in claim 1, wherein said tannin-rich mixed substrate comprises myrobalan fruit powder (*Terminalia chebula*) and gallo seed cover powder (*Caesalpinia digyna*) in a proportion of 1:3 to 1:⅓.

3. The process as claimed in claim 1, wherein said culture medium is a modified Czapek-Dox medium.

4. The process as claimed in claim 3, wherein the modified Czapek-Dox medium comprises tannic acid as a carbohydrate source.

5. The process as claimed in claim 1, wherein the substrate and culture medium are present in a ratio of 0.2:1 to 0.8:1.

6. The process as claimed in claim 1, wherein the fungi are maintained on a 2% malt extract agar slant.

7. The process as claimed in claim 1, wherein the induced innoculum is obtained by providing a tannic acid substrate in Czapek-Dox medium, sterilizing the tannic acid substrate; and inoculating the substrate with a spore suspension of the fungi *Rhizopus oryzae* and *Aspergillus foetidus* to obtain an inoculated substrate; and incubating the inoculated substrate to obtain an induced innoculum.

8. The process as claimed in claim 1, wherein an induced innoculum containing $1\times10$ spores/ml to $2\times10^8$ spores per ml is added to 20 gins of the mixed substrate.

9. The process as claimed in claim 1, wherein the organic solvent is ethyl acetate.

10. The process as claimed in claim 1, which further includes the steps of adding water to the culture medium and the fermented mass; heating at a temperature in the range of 60–70° C. to obtain an aqueous solution of gallic acid, extracting the aqueous solution of gallic acid with an organic solvent to obtain a solution of the gallic acid in the organic solvent, followed by evaporation of the solvent to obtain gallic acid.

11. The process as claimed in claim 10, wherein the organic solvent is ethyl acetate.

12. The process as claimed in claim 10, which further includes an additional extraction step comprising using a second different solvent, to form a solution of gallic acid in said second solvent.

13. The process as claimed in claim 12 wherein the second different solvent is ethyl ether.

14. The process as claimed in claim 1, wherein the ratio of the fungi *Rhizopus oryzae* and *Aspergillus foetidus* ranges from between 0.25:1 to 1:1.

15. A process for the preparation of gallic acid comprising:

providing a tannin-rich mixed substrate and a culture medium, in a liquid medium, wherein said tannin-rich mixed substrate comprises myrabalan fruit powder (*Terminalia chebula*) and gallo seed cover powder (*Caesalpinia digyna*) in a proportion of 1:3 to 1:1/3;

adding an induced innoculum comprising the fungi *Rhizopus oryzae* and *Aspergilus foetidus* to said substrate to obtain a fermented mass and gallic acid, wherein the ratio of the fungi *Rhizopus oryzae* and *Aspergillus foetidus* ranges from 0.25:1 to 1:1;

extracting gallic acid from the culture medium and the fermented mass using an organic solvent; and evaporating the organic solvent to obtain gallic acid.

* * * * *